(12) United States Patent
Broderick et al.

(10) Patent No.: US 7,208,288 B2
(45) Date of Patent: Apr. 24, 2007

(54) METHODS FOR ENHANCING THE LYSIS OF COAGULATED BLOOD WITH APOLIPOPROTEIN E2 PHENOTYPE

(76) Inventors: Joseph P. Broderick, MSB 4314, University of Cincinnati, P.O. Box 670525, Cincinnati, OH (US) 45267-0525; Joseph F. Clark, Neurology Ventz 2326, University of Cincinnati, P.O. 670525, Cincinnati, OH (US) 45267-0525; Daniel Woo, 8355 Miami Rd., Cincinnati, OH (US) 45243

( * ) Notice: Subject to any disclaimer, the term of this patent is extended or adjusted under 35 U.S.C. 154(b) by 650 days.

(21) Appl. No.: 10/398,880

(22) PCT Filed: Oct. 12, 2001

(86) PCT No.: PCT/US01/42719

§ 371 (c)(1),
(2), (4) Date: Jul. 17, 2003

(87) PCT Pub. No.: WO02/30359

PCT Pub. Date: Apr. 18, 2002

(65) Prior Publication Data

US 2004/0006017 A1    Jan. 8, 2004

Related U.S. Application Data

(60) Provisional application No. 60/240,407, filed on Oct. 13, 2000.

(51) Int. Cl.
*C12Q 1/56* (2006.01)
(52) U.S. Cl. .................. 435/13; 424/94.64; 436/69; 514/2; 514/21; 514/822; 530/368.25

(58) Field of Classification Search ............... None
See application file for complete search history.

(56) References Cited

U.S. PATENT DOCUMENTS

| 6,046,381 A | 4/2000 | Mucke et al. |
| 6,313,089 B1 | 11/2001 | Matthew et al. |
| 2004/0102374 A1* | 5/2004 | Broderick et al. ............ 514/12 |

OTHER PUBLICATIONS

Shuvaev V., et al, Glycation of Apolipoprotein E Impairs Its Binding to Heparin: Identification of the Major Glycation Site. Biochimica et Biophysica Acta. Mar. 1999. vol. 1454, No. 3, pp. 296-308.

* cited by examiner

*Primary Examiner*—Ralph Gitomer
(74) *Attorney, Agent, or Firm*—Dinsmore & Shohl LLP; Denise M. Everett

(57) ABSTRACT

Methods for enhancing the lysis of coagulated blood comprise administering to coagulated blood a combination of clot clysis agent and a lysis enhancing amount of apolipoprotein E2 (Apo E2) or a therapeutic derivative thereof. Methods for reducing the risk of blood coagulation comprise administering to blood a combination of a clot lysis agent and a lysis enhancing amount of Apo E2 or a therapeutic derivative thereof. Additional methods for enhancing the lysis of coagulated blood comprise administering to an individual a specific level of clot lysis agent wherein the specific level is based upon the apolipoprotein phenotype of the individual. Further methods for reducing the risks of blood coagulation comprise administering to blood a specific level of a clot lysis agent wherein the specific level is based upon the apolipoprotein phenotype of the individual.

13 Claims, 5 Drawing Sheets

METHODS FOR ENHANCING THE LYSIS OF COAGULATED BLOOD WITH APOLIPOPROTEIN E2 PHENOTYPE

This application is filed as a 371 application based on PCT/US01/42719 filed Oct. 12, 2001 which claims benefit of Ser. No. 60/240,407 filed Oct. 13, 2000.

GOVERNMENT INTERESTS

This invention was made, at least in part, with funds from the Federal Government, awarded through NIH grants: NO1-NS-02382, NO1-NS-02374, NO1-NS-02377, NO1-NS-02379, NO1-NS-02373, NO1-NS-02378, NO1-NS-02376, NO1-NS-02380, and NIH RO1 HL67186-01. The US government therefore has certain acknowledged rights to the invention.

FIELD OF THE INVENTION

This invention relates to methods for enhancing the lysis of coagulated blood and to methods for reducing the risk of blood coagulation by administration of a clot lysis agent and apolipoprotein E2. The invention further relates to methods for enhancing the lysis of coagulated blood and methods for reducing the risk of blood coagulation by administration of a specific level of clot lysis agent based upon the apolipoprotein phenotype of the individual.

BACKGROUND OF THE INVENTION

Thrombolytic therapy is a term known generally to reference treatment procedures for individuals with ischemic diseases or other perfusion disorders. Many thrombolytic therapies comprise administering a clot lysis agent to affect the lysis of coagulated blood, i.e. blood clots. Various clot lysis agents and their associated therapeutic derivatives are known to be effective to stimulate the lysis of coagulated blood. Clot lysis agents known to enhance the lysis of coagulated blood include, but are not limited to, TNK-t-PA. tissue plasminogen activator (t-PA), reteplase, streptokinase, heparin, coumadin, GIIb IIIa receptor blockers, and their therapeutic derivatives or mixtures. These agents are also known for use in reducing the risk of undesirable blood coagulation in individuals having a tendency or risk of excessive blood clotting.

For example, the administration of a clot lysis agent such as t-PA within several hours following a stroke is useful in the lysis of blood clots for an individual suffering from an ischemic disease, such as ischemic stroke. t-PA and/or other clot lysis agents may also be administered to reduce the risk of undesirable blood clotting, for example during angiographic catheter procedures.

As undesirable blood coagulation can occur in connection with a number of different conditions, for example, angina, acute stroke, acute myocardial infarction, peripheral arterial occlusion, pulmonary embolism, and venous thrombosis, there is a continuing need to advance and improve current therapeutic treatments in both prophylactic and interventional therapies.

SUMMARY OF THE INVENTION

Accordingly, it is an object of the present invention to provide novel methods for enhancing the lysis of coagulated blood and/or for reducing the risk of blood coagulation, i.e. undesirable or excessive clotting. It is a further object of the present invention to provide methods for enhancing the lysis of coagulated blood and/or for reducing the risk of blood coagulation which may be used in place of prior art therapies.

These and additional objects are provided by the present invention. More particularly, in one embodiment, the invention is directed to methods for enhancing the lysis of coagulated blood, which methods comprise administering to coagulated blood a combination of a clot lysis agent and a lysis enhancing amount of apolipoprotein E2 (Apo E2) or a therapeutic derivative thereof.

The invention is further directed to methods for reducing the risk of blood coagulation. These methods comprise administering to blood a combination of a clot lysis agent and a lysis enhancing amount of Apo E2 or a therapeutic derivative thereof.

In a further embodiment, the invention is directed to methods for enhancing the lysis of coagulated blood by administering a specific level of a clot lysis agent. The specific level of clot lysis agent to be administered to the individual is based upon the apolipoprotein phenotype of the individual.

In yet a further embodiment, the invention is directed to methods for reducing the risk of blood coagulation by administering a specific level of a clot lysis agent wherein the specific level is based upon the apolipoprotein phenotype of the individual.

The methods according to the present invention are advantageous in the treatment of ischemic diseases by enhancing the lysis of coagulated blood and/or reducing the risk of excessive, undesirable blood clotting, particularly in individuals at risk of exhibiting excessive or undesirable blood clotting.

These and additional aspects, objects and advantages of the invention are more fully described in the detailed description.

BRIEF DESCRIPTION OF THE DRAWINGS

The following detailed description will be more fully understood in view of the accompanying drawings in which.

DETAILED DESCRIPTION

Figure 1:
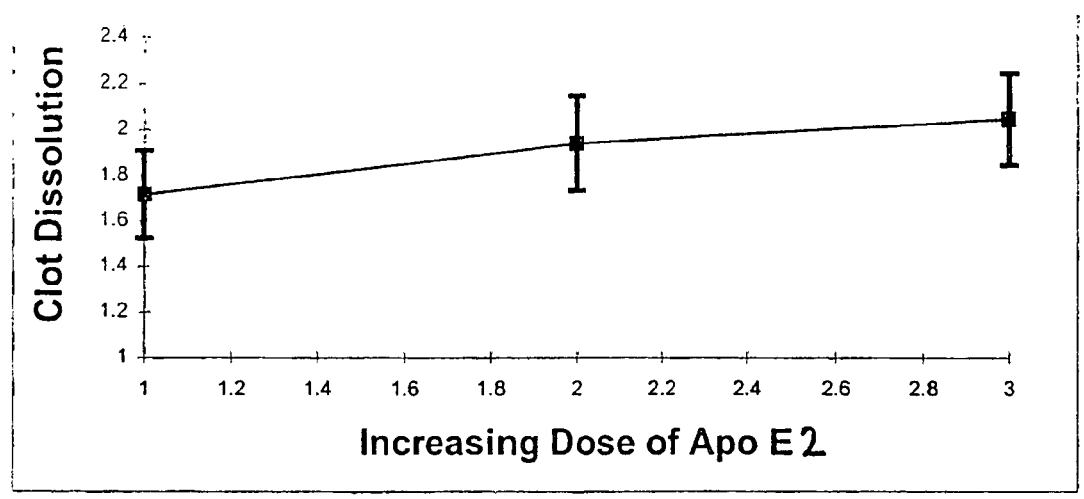
FIG. 1 depicts an enhancing effect of clot lysis in vitro through the administration of t-PA and Apo E2 as described in Example 2.

The present invention is directed to methods for enhancing the lysis of coagulated blood by administering to coagulated blood a combination of a clot lysis agent and a lysis-enhancing amount of apolipoprotein E2 (Apo E2) or a therapeutic derivative thereof. This invention also is directed to methods for reducing the risk of undesirable elevated levels of coagulated blood by administering to blood a combination of a clot lysis agent and a lysis-enhancing amount of Apo E2 or a therapeutic derivative thereof.

Current thrombolytic therapies are premised upon the administration of a clot lysis agent to lyse coagulated blood, for example after an ischemic disease is detected, or to prevent clot formation by administration of a clot lysis agent. In addition to improving upon previous thrombolytic therapy procedures, this invention is also directed to methods for enhancing the lysis of coagulated blood and to methods for reducing the risk of blood coagulation before formation by administering a specific level of clot lysis agent, wherein the specific level is based upon the apolipoprotein phenotype of the individual to be treated. By determining the apolipoprotein phenotype expressed by an individual, and particularly by determining if an individual expresses Apo E2, a physician or care-giver will be able to predict if enhancement of an administered agent will occur as a result of the individual's inherent phenotype, and therefore more accurately dose the clot lysis agent in an amount suitably specific for the individual.

As used herein, "lysis of coagulated blood" generally refers to the dissolution or destruction of a blood clot or thrombus. As used herein, "coagulated blood" generally refers to a clot of blood such that the blood is in the form of a soft semisolid or solid mass. As used herein, administering a clot lysis agent in "combination" with a lysis enhancing amount of apolipoprotein E2 or a therapeutic derivative of E2 generally refers to administering the products together, i.e., simultaneously, or in conjunction with one another, i.e., sequentially. "Clot lysis agent" generally refers to any of the known thrombolytic agents which are used to enhance the lysis of blood clots. Known agents include, but are not limited to, TNK-t-PA, t-PA, reteplase, streptokinase, heparin, coumadin, GIIb IIIa receptor blockers, therapeutic derivatives thereof, or mixtures thereof. Preferably, the clot lysis agent comprises tissue plasminogen activator (t-PA) or a derivative thereof.

Apolipoprotein E (Apo E) is known generally as a member of a family of lipid-associated proteins whose isoforms have been implicated as an important modifier of several neurologic, vascular and cardiovascular diseases. See Corder, et al. Science; 261:921–3 (1993). Apo E has three common isoforms —E2, E3, and E4. These monomeric isoforms combine to make six Apo E phenotypes: E2/2, E2/3, and E2/4 (referred to as the E2 category), E3/3 (E3 category), and E4/3 and E4/4 (E4 category). See Payami, et al. JAMA; 271:1316–7 (1994); Polvikoski, et al. N Engl J Med; 333:1242–1247 (1995). The E2 isoforms, E2/2, E2/3 and E2/4, refened to herein as Ape E2, are employed in the methods of the invention. Therapeutic derivatives, for example fragments of Apo E2 having the lysis enhancing activity, can also be administered.

As used herein, "therapeutic derivative" generally refers to an Apo E2 fragment or chemical or structural analogue exhibiting the lysis-enhancing activity. For example, as is known in the art, one can isolate an Apo E protein and selectively degrade the protein to smaller peptides which are then screened to determine if they contain the lipophilic regions of the Apo E2 protein known to exhibit lipophilic properties. Reference is made to the NIH National Library of Medicine for further details of the Apo E2 protein and degradation and screening techniques for obtaining such derivatives. These therapeutic derivatives will be able to perform the lysis-enhancing activities exhibited by the Apo E2 protein, and thereby can be administered in conjunction with a lysis agent, such as t-PA to enhance the lytic behavior.

The dosages of conventional clot lysis agents are generally based upon the individual's physiological characteristics and given medical condition. Typically a patient can be administered, for example, a range of t-PA of from about 0.1–10.0 mg/kg of blood. A standard therapeutic dose of t-PA physiologically appropriate for thrombolytic therapy to be administered intravenously to blood over a one hour period is 0.9 mg/kg of blood. "Lysis enhancing amount" generally refers to a quantitative amount of Apo E2 with which enhanced lysis activity of a conventional clot lysis agent is demonstrated. Suitable doses of Apo E2, or its therapeutic derivative, necessary to enhance the lytic activity of a clot lysis agent such as t-PA will vary depending, inter alia, on physiological characteristics of the individual to be treated, including, but not limited to the Apo E phenotype of the individual, and on the given medical condition of the individual. However, typically, the Apo E2 or derivative is administered in an amount of about equal molar stoicheometry with the clot lysis agent to provide the lytic enhancing activity. The equimolar amount is based on the amount of clot lysis agent administered and any additional amount of clot lysis agent inherent in the blood. For example, human blood typically contains about 0.0009 mg/l t-Pa; this inherent amount would typically not influence the amount of Apo E or derivative which is administered. "Ischemic disease" generally refers to a medical condition causing or resulting in a decrease in blood supply to a bodily organ, tissue, or location due to constriction or obstruction of blood vessels. Examples of ischemic diseases comprise myocardial infarction, unstable angina, coronary artery thrombus, and peripheral vascular disease. "Peripheral vascular diseases" typically refer to, inter alia, occlusions, retinopathy, and organ embolisms. "Organ embolism" typically refers to the obstruction or occlusion of a blood vessel by an embolus within an organ system, for example, such as a pulmonary embolism. In treating these and similar ischemic diseases, thrombolytic therapy in the form of a clot lysis agent is often administered to enhance the lysis of coagulated blood. For instance, some diseases and procedures that may be effected by such thrombolytic therapy include, angina, TIA pulmonary embolism arteriosclerosis heart attack, surgery, vascular surgery, grafts, organ transplants, limb reattachment, trauma pregnancy, child birth and post partum. The methods for enhancing the lysis of coagulated blood or for reducing the risk of undesirable or excessive clot lysis according to the present invention may be employed in treatment of any such diseases or conditions.

In one embodiment, the clot lysis agent and the Apo E2 are administered to an individual with an ischemic disease to enhance lysis of blood coagulation associated with the disease.

In one specific embodiment, the clot lysis agent and the lysis-enhancing amount of Apo E2 are administered to reduce an individual's elevated level of coagulated blood. In determining that an individual has an elevated level of coagulated blood, these methods may be administered to reduce the level of blood coagulation associated with an ischemic disease.

In yet another embodiment, methods of reducing the risk of blood coagulation can be administered, particularly in individuals at risk of developing undesirable or excessive clotting of blood. These methods comprise administering to blood a combination of a clot lysis agent and a lysis-enhancing amount of Apo E2 or a therapeutic derivative thereof. For example, the combination can be administered to reduce the risk of the formation of an angiographic catheter clot.

In a further embodiment, a specific level of clot lysis agent is administered wherein the specific level is based upon the apolipoprotein phenotype of the individual. In determining the specific level of clot lysis agent to administer to the individual, the apolipoprotein phenotype of the individual will help the physician or care-giver conclude how much clot lysis agent will be required to obtain desired results. For example, less clot lysis agent will typically be required if the individual has an Apo E2 phenotype due to the clot lysis enhancing properties exhibited by the natural Apo E2. Preferably, the individual's apolipoprotein phenotype is determined prior to administering the specific level of clot lysis agent. Methods for determining apolipoprotein phenotype from blood or serum samples are known in the art and may be employed.

In another specific embodiment, the clot lysis agent and the lysis-enhancing amount of Apo E2 are administered to an individual with post surgical complications of occlusion or clotting to enhance lysis of blood coagulation associated with the ischemic disease. Furthermore, a specific level clot lysis agent can be administered to an individual based upon the apolipoprotein phenotype of the individual to enhance the lysis of coagulated blood associated with post surgical complications of occlusion or clotting.

The following examples are provided to illustrate the methods and various embodiments of the present invention. While the examples utilize t-PA as the clot lysis agent, similar results can be obtained with other clot lysis agents as mentioned above. The use of similar clot lysis agents will be apparent to one of ordinary skill in the art and are within the scope of the claims.

EXAMPLE 1

The present example demonstrates the correlation of efficacy between Apo E2 and a clot lysis agent such as t-PA. This example extended the study of results previously reported for the NINDS t-PA Stroke Study, which consisted of two sequential placebo-controlled, randomized, double-blind, multi-center clinical trials. See NINDS rt-PA Stroke Study Group. New Engl J Med; 333:1581–1587 (1995); Brott, et al. Stroke; 20:864–70 (1989). Of the 624 individuals participating within the NINDS Study, 409 individuals with a serum sample available were used as a study group in this example to demonstrate the enhanced lysis activity provided by a combination of Apo E2 and a clot lysis agent. Of the 409 individuals, 217 were treated with t-PA while the remaining 192 were given a placebo. The phenotypes for the 409 individuals, determined for the purpose of the study described herein, were as follows: Apo E2-2 (1%), Apo E2-3 (12%), Apo E2-4 (1%), Apo E3-3 (60%), Apo E3-4 (24%), and Apo E4-4 (2%).

Statistical Analysis:

To investigate the relationship of the Apo E2 phenotypes with clinical outcome measures, an analysis for each individual clinical outcome for all placebo and t-PA treated individuals was performed and included treatment assignment as a covariate. The analyses that examined the relationship of the Apo E2 phenotype and the risk of intracerebral hemorrhage (ICH) within 36 hours of treatment onset were carried out initially using the t-PA treated group only and subsequently using both t-PA and placebo-treated individuals. A logistic regression model was carried out for a single binary outcome, e.g., Barthel Index 95 or 100 (yes, no). In addition, the Generalized Estimating Equations approach (GEE) was used to assess the effects of Apo E2 on a binary measure of favorable outcome based on all four clinical outcome measures. See Tilley, et al. Stroke 1996; 27:2136–42. An interaction between Apo E2 and treatment was considered significant if the p-value for interaction was ≦0.10. See Fleiss. Controlled Clinical Trials; 7:267–275 (1986). (In all analyses of interactions, the main effects that are combined to form the interaction are included in the model). If no interaction was detected. It was assumed that the effect of Apo E2 was the same for t-PA or placebo-treated individuals. Detection of an interaction indicated that the effect of treatment (the efficacy of t-PA as compared to placebo) depended upon the presence or absence of an Apo E2 phenotype. The log-rank test was used to test the effect of an Apo E2 phenotype with respect to the deaths in 90 days, after adjusting for the treatment variable.

In analyzing the effect of the Apo E2 phenotype on CT-lesion volumes at 3 months, a Poisson regression model was used on the cube-root transformed CT-lesion volume to reduce the skewness and variability. See NINDS rt-PA Stroke Study Group. Stroke;29:287 (1998). A negative coefficient indicated a reduction of CT-lesion volume in the presence of the Apo E2 phenotype compared to the absence of the Apo E2 phenotype or a reduction in CT-lesion volume in t-PA treated individuals as compared to the placebo-treated individuals. The median and inter-quartiles of CT lesion volume were reported as descriptive analyses.

All the above mentioned analyses were then re-run adjusting for a) the baseline variables unbalanced between t-PA and placebo as well as the baseline variables associated with the presence of the Apo E2 phenotypes, b) the baseline variables known to be significantly related to three-month outcome in the previously reported models of outcome using the entire NINDS t-PA Stroke Trial cohort. See NINDS t-PA Stroke Study Group. Stroke;28:2109–2118 (1997); NINDS t-PA Stroke Study Group. Stroke; 28:2119–2125 (1997); and NINDS rt-PA Stroke Study Group. Stroke; 29:287 (1998). A time-from-stroke-onset-to-treatment by the treatment interaction was also added into the model for 3-month favorable outcome based upon previously demonstrated interaction of time and efficacy of t-PA therapy.

For descriptive purposes, the adjusted log odds and 95% confidence intervals are presented comparing each Apo E2/treatment category (i.e. "Apo E2 (+)/Treatment (+)", "Apo E2 (+)/Treatment(−)", "Apo E2(−)/Treatment(+)" to the reference group "Apo E2(−)/Treatment(−)".

The serum patient samples had been stored a median time of 38 months. Since patient serum (and not white blood cells) was available for analysis, patient DNA is not used for the laboratory test. The method described herein has been demonstrated to have a 98% concordance rate with Apo E genotypes in 431 samples of patients that underwent genotyping. See Kataoka et al, *Clinical Chemistry* 1994; 40:11–13.

Table 1a shows the analysis of 3-month outcomes by treatment and by Apo E2 phenotype (yes (+)/no(−)) categories for the individual and global tests without adjusting for any covariates. In placebo individuals, Apo E2 itself was not associated with any of the 3-month favorable outcomes (p-values >0.42), but there was an interaction between t-PA treatment and Apo E2 phenotype (p-value =0.03). Individuals treated with t-PA who had an Apo E2 phenotype had a much greater likelihood of a favorable outcome by any of the four 3-month measures (range of odds ratios from 3.6–6.3) as compared to those individuals treated with placebo and without an E2 phenotype. Individuals treated with t-PA who did not have an Apo E2 phenotype had a slightly higher likelihood of a favorable outcome by any of the four 3-month measures (range of odds ratios from 1.6–2.0) as compared to those treated by placebo and without an E2 phenotype.

TABLE 1a 3-month outcome by Apo E2 status without adjusting for baseline covariates

| | t-PA | | Placebo | | |
|---|---|---|---|---|---|
| Outcome | Apo E2 (+) N = 27 | Apo E2 (−) N = 190 | Apo E2 (+) N = 31 | Apo E2 (−)* N = 161 | P-values for |
| NIHSS = 0 or 1% | 63 | 33 | 19 | 21 | 0.04 |
| OR | 6.3 | 1.8 | 0.9 | 1.0 | |
| 95% Cl | 2.7, 15.1 | 1.1, 2.9 | 0.3, 2.4 | NA | |
| Barthel = 95 or 100% | 70 | 52 | 39 | 40 | 0.16 |
| OR | 3.6 | 1.6 | 1.0 | 1.0 | |
| 95% Cl | 1.5, 8.7 | 1.1, 2.5 | 0.4, 2.1 | NA | |
| Rankin = 0 or 1% | 67 | 43 | 23 | 27 | 0.06 |
| OR | 5.5 | 2.0 | 0.8 | 1.0 | |
| 95% Cl | 2.3, 13.1 | 1.3, 3.2 | 0.3, 2.0 | NA | |
| Glasgow = 1% | 67 | 46 | 35 | 30 | 0.29 |
| OR | 4.6 | 1.9 | 1.3 | 1.0 | |
| 95% Cl | 1.9, 10.9 | 1.2, 3.0 | 0.6, 2.8 | NA | |
| Global | | | | | 0.03 |
| OR | 5.4 | 1.8 | 1.0 | 1.0 | |
| 95% Cl | 2.4, 12.1 | 1.2, 2.6 | 0.5, 2.0 | NA | |

*Reference groups for calculation of odds ratio

As seen by Table 1b, the interaction between treatment and Apo E2 phenotype persisted after adjusting for imbalances in baseline variables between treatment groups and between individuals with and without an Apo E2 phenotype, as well as adjusting for baseline variables previously associated with a favorable outcome at three months (p=0.01). The likelihood of a favorable outcome by any of the four 3-month measures for individuals who were t-PA treated and with an Apo E2 phenotype became even higher (range of odds ratio from 4.0–8.1) as compared to those without an E2 phenotype treated by placebo. When adjusted for a time-from-stroke-onset-to-treatment by the treatment interaction that was previously identified, the interaction between Apo E2 and treatment also remained (p=0.03).

TABLE 1b 3-month outcome by Apo E2 status adjusted for baseline covariates**

| | t-PA | | Placebo | | |
|---|---|---|---|---|---|
| Outcome | Apo E2 (+) N = 27 | Apo E2 (−) N = 190 | Apo E2 (+) N = 31 | Apo E2 (−)* N = 161 | P-values for |
| NIHSS = 0 or 1% | 63 | 33 | 19 | 21 | 0.08 |
| OR | 7.4 | 2.0 | 0.9 | 1.0 | |
| 95% Cl | 2.1, 25.8 | 1.1, 3.6 | 0.3, 2.8 | NA | |
| Barthel = 95 or 100% | 70 | 52 | 39 | 40 | 0.31 |
| OR | 4.8 | 2.1 | 1.0 | 1.0 | |
| 95% Cl | 1.4, 16.8 | 1.2, 3.7 | 0.4, 2.7 | NA | |
| Rankin = 0 or 1% | 67 | 43 | 23 | 27 | 0.05 |
| OR | 8.1 | 2.2 | 0.6 | 1.0 | |
| 95% Cl | 2.1, 31.4 | 1.2, 4.1 | 0.2, 2.0 | NA | |
| Glasgow = 1% | 67 | 46 | 35 | 30 | 0.49 |
| OR | 4.0 | 2.2 | 1.0 | 1.0 | |

TABLE 1b-continued 3-month outcome by Apo E2 status adjusted for baseline covariates**

| | t-PA | | Placebo | | |
|---|---|---|---|---|---|
| Outcome | Apo E2 (+) N = 27 | Apo E2 (−) N = 190 | Apo E2 (+) N = 31 | Apo E2 (−)* N = 161 | P-values for |
| 95% Cl | 1.2, 13.6 | 1.3, 4.0 | 0.4, 2.9 | NA | |
| Global | | | | | 0.01 |
| OR | 6.4 | 2.0 | 0.8 | 1.0 | |
| 95% Cl | 2.7, 15.3 | 1.2, 3.2 | 0.4, 1.7 | NA | |

*Reference groups for calculation of odds ratio
**Baseline covariates: Age (categorized), Rank of the actual weight, Rank of total dose delivered, Baseline pulse pressure, Prior aspirin use, NIHSS (5 groups), Hypertension, Race, Cardiac history, Age × NIHSS. Admission mean blood pressure (MBP), Age × Admission MBP, Diabetes and the variable: early CT finding.

In looking at the relationship of the Apo E2 phenotype to intracerebral hemorrhage (ICH), no interactions were detected with respect to symptomatic ICH or all ICH within 36 hours of treatment onset (p-values>0.40). The Apo E2 phenotype was not significantly associated with either symptomatic ICH or with all ICH, even after adjustments for the other covariates in the primary hemorrhage model or the covariates unbalanced between groups with and without an Apo E2 phenotype (p-values >0.30). See NINDS t-PA Stroke Study Group. *Stroke;*28:2109–2118 (1997).

In determining the relationship between the Apo E2 phenotype and mortality at three months, no interactions were detected. The mortality rate at 90 days was 17% in individuals with an Apo E2 phenotype vs. 19% in individuals without an Apo E2 phenotype (p-value=0.66), adjusting for treatment status. After adjusting for the variables unbalanced between the t-PA and placebo treatment groups, and variables associated with outcome, the results remained the same.

In determining the relationship between Apo E2 phenotype and CT lesion volumes at 24 hours and at 3 months, of the 409 individuals in this extended study, 404 individuals had a lesion volume for determination of 3-month outcomes. Individuals with an Apo E2 phenotype had a smaller median CT-lesion volume (8.5 cm$^3$, interquartile range of 1.0 to 36.0 cm$^3$) as compared to individuals without an Apo E2 phenotype (20.0 cm$^3$, interquartile range of 2.0 to 99.0 cm$^3$). However, no interaction between Apo E2 status and treatment on 3-month CT-lesion volume was detected after adjusting for imbalances in baseline variables and for the other covariates associated with CT-lesion volume in a previously reported model (age, age ×treatment interactions baseline NIHSSS, early CT findings of ischemia, old CT-lesion volume at baseline, an NIHSS×early CT findings ischemia interaction, an NIHSS×old CT-lesion volume interaction, and presumptive stroke subtype).

It was also determined whether the 409 individuals who had blood samples available for analysis were comparable to the 215 individuals without a blood sample in the NINDS t-PA Trial cohort. To make this determination, thirty-five variables, including time of stroke onset to treatment were selected. To determine if there were significant differences between individuals with and without a blood sample, a chi-square test for categorical variables (or Fisher's exact test if a cell proportion was too small) and a t-test or Wilcoxon test for continuous variables was used, depending on whether the variable was normally distributed. The observations described herein of increased efficacy of a clot lysis agent, such as t-PA, in individuals with an Apo E2 phenotype is unexpected and significant

EXAMPLE 2

In this example, the lysis enhancing effect of Apo E2 is further demonstrated in vitro. There are various methods for determining the function, action and or kinetics of t-PA. These include but are not limited to: measuring fibrin degradation fragments, clot lysis, clot weight, fluid evolution weight, clot times and others. Those experienced in the art will be familiar with these and other methods for assaying t-PA activity or clot degradation/formation etc. The data from this study consists of a measurement of clot dissolution or lysis by measuring the amount of liquid liberated from the blood sample. This is an index of clot lysis and the clot lysis is stimulated by t-PA.

Typically, two mls of fresh human blood are drawn and added to pre-weighed vials containing known amounts of t-PA with or without Apo E2. The blood is mixed and allowed to equilibrate for 40 minutes. The vials are centrifuged at 1g for 15 minutes and the supernatant decanted. Clot weight and solution weight is determined and used to measure clot degradation or dissolution. Increasing supernatant volumes indicate increased clot degradation or increasing clot dissolution.

FIG. 1 (N=3 for each) depicts the enhancing effect of clot lysis on blood from a first individual through the increasing administration of Apo E2. As described above, the normal therapeutic dosage of t-PA administered to individuals for thrombolytic therapy such as antistroke is 0.9 mg/kg (0.9 mg/l) of blood given intravenously over one hour. The blood in this example was given a dose of t-PA at 1 mg/l with increasing dosages of Apo E2 in micrograms/l. The y-axis represents the rate of clot dissolution. As shown by the x-axis, increasing dosages of Apo E2 resulted in the enhancement of lytic behavior.

Figure 2:
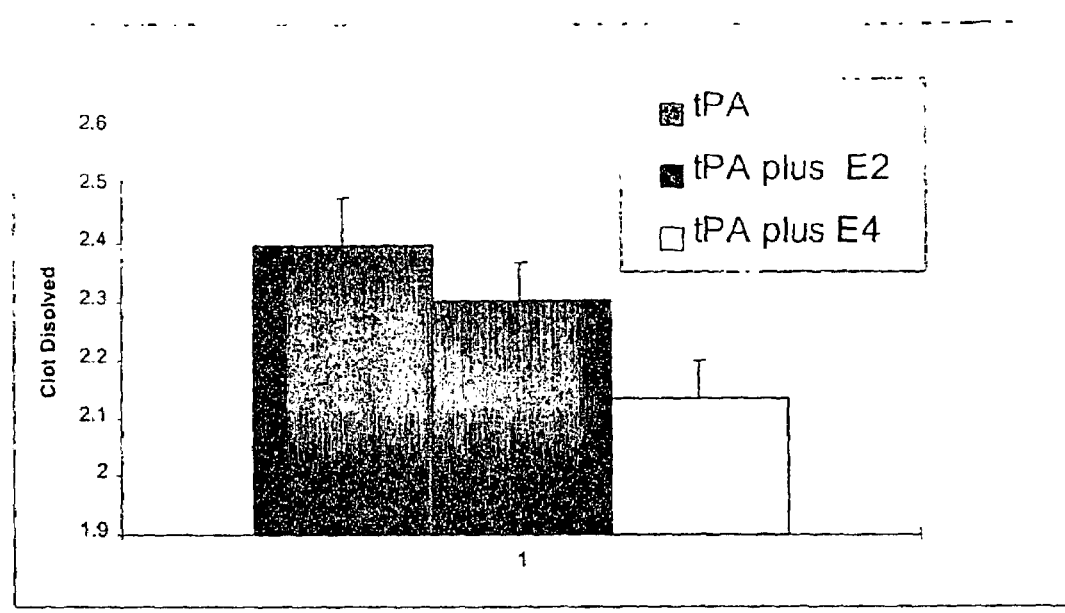
FIG. 2 depicts effects of clot lysis in vitro with respect to t-PA administration in conjunction with Apo E2 or Apo E4 as described in Example 2.

FIG. 2 (N=3 for each) depicts the effect of clot lysis on the blood from a second individual with respect to t-PA administration in combination with Apo E2 or Apo E4. The y-axis demonstrates in grams (g) the amount of clot lysis or dissolution measured. The administration of t-PA alone at a level of 0.5 mg/l blood shows that the level of clot lysis was substantially complete at 2.5 g. Upon administration of t-PA in conjunction with Apo E2, no significant change in lytic activity was recognized. This result was likely caused due to the individual's administration of aspirin or similar lytic agent before the blood sample was performed. The amount of clot lysis was significantly inhibited, however, upon the administration of t-PA in conjunction with Apo E4. The lysis inhibiting aspects of Apo E4 are disclosed in the inventors' application entitled Methods for Controlling the Lysis of Coagulated Blood with Apolipoprotein E4 (Apo E4), filed on even date herewith.

EXAMPLE 3

In this example, the lipophilic interaction of t-PA with Apo E2 is demonstrated through Thin Layer Chromatography (TLC). There are numerous analytical methods for measuring molecular interactions. These are known to those experienced in the art and include, but are not limited to TLC, Paper Chromatography, electrophoresis, diffraction methods, Nuclear Magnetic Resonance, and other methods.

A known concentration of t-PA in a first prepared solution is applied to a TLC plate and allowed to dry to measure molecular interaction. In a second solution equal molar amounts of t-PA and Apo E2 are employed and the solution is similarly applied to a second TLC plate and allowed to dry.

Figure 3:
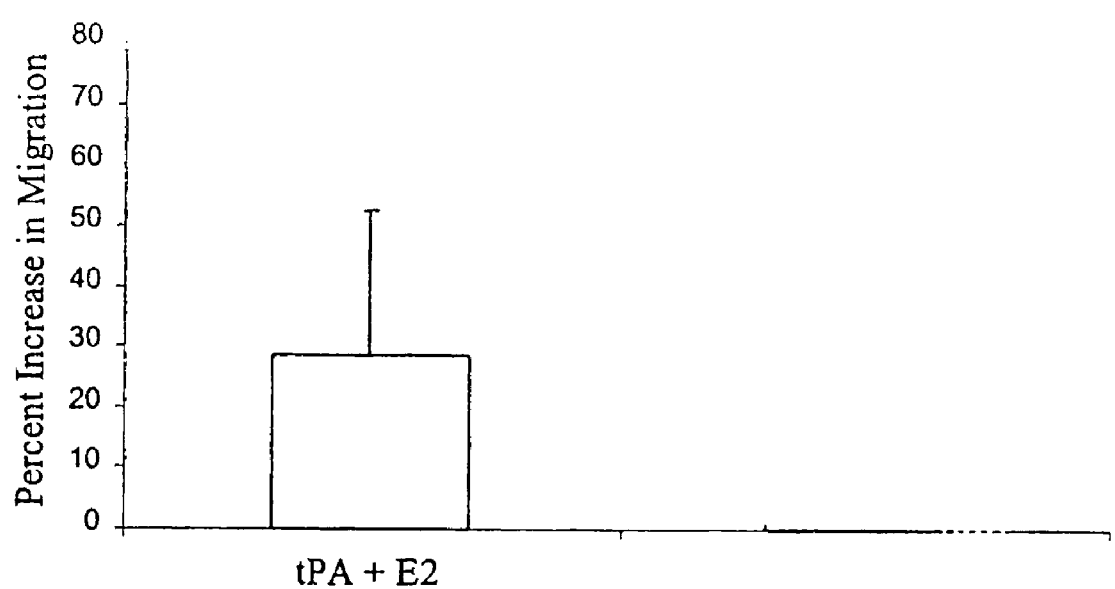
FIG. 3a depicts a lipophilic interaction of t-PA with Apo E2 observed by Thin Layer Chromatography (TLC) as described in Example 3.
FIG. 3b depicts a hydrophobic interaction of t-PA with Apo E4 observed by Thin Layer Chromatography (TLC) as described in Example 4.

The TLC plates are put into migration chambers containing chloroform:ethanol in a 3:1 or 1:1 ratio and allowed to migrate until the solvent front approaches 1 cm from the top of the plate. The plates are removed from the chambers and allowed to dry in the fume cupboards. The plates can be read with ninhydrin or uv light quenching. The migration distances are marked and rf values reported. The plate to which the first solution containing only t-PA is applied is used as a reference and the percent increase in migration exhibited by the second solution is set forth in FIG. 3a (N=3 for each).

The results demonstrate that Apo E2 reacts and uniquely binds with t-PA under the given conditions., presumably through the lipophilic protein properties although the inventors do not intend to be bound by this theory. For example, the Apo E2 dimer can form a complex with amyloid beta peptide more efficiently than the other Apo isoforms. Furthermore, as it has previously been shown. Apo E2 can stimulate endohelial production of heparin sulfate, whereby heparin may enhance the lytic effect of t-PA in stroke patients. See del Zoppo et al, *Stroke* 29: 4–11 (1998).

EXAMPLE 4

In this example, using an in vitro clot degradation method, the lysis enhancing and stimulating effect of Apo E2 on t-PA is further demonstrated. The effect is seen as a decrease of the $EC_{50}$ for t-PA induced clot lysis.

The ability of Apo E isoproteins to modulate t-PA induced clot lysis is assessed using an in vitro clot assay system. This system uses the decrease in clot formation in the presence of t-PA to approximate the amount of clot lysis. Blood samples are obtained from 18 volunteers and divided into three Apo E genotypes (6 patients in each group): E2 (E2/E2, E2/E3, E2/E4), E3 (E3/E3) and E4 (E3/E4, E4/E4). Clot lysis in the presence of varying concentrations of t-PA (0 to 4 μg/ml), is assessed in the presence or absence of supplemental Apo E2, E3 or E4 (9.8 μg/ml) for each patient genotype. The results are expressed as $EC_{50}$s, which are the effective concentrations of t-PA required to achieve 50% lysis of the clot.

Figure 4:
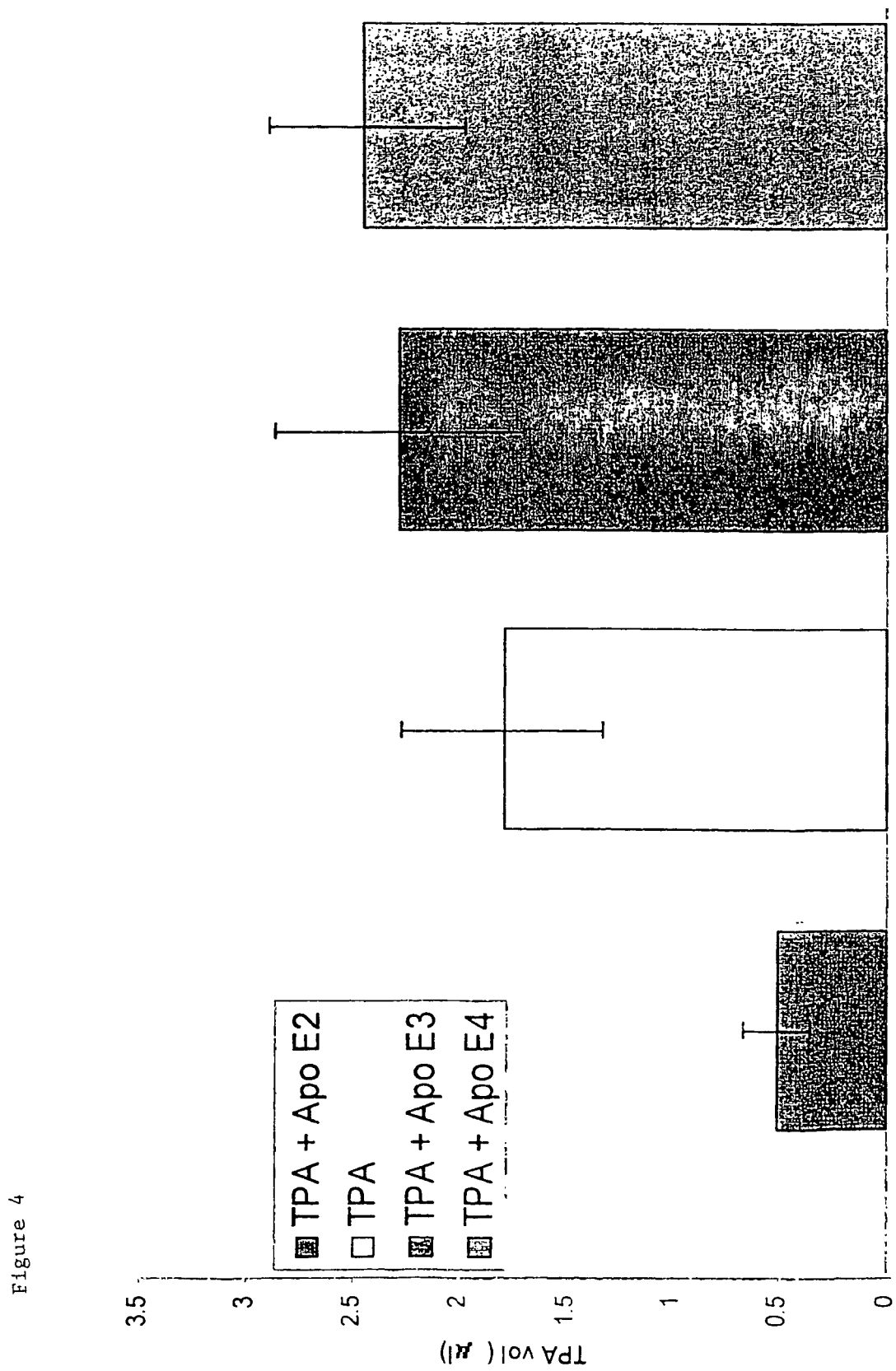
FIG. 4 depicts the average $EC_{50}$ clot dissolution of t-PA in conjunction with Apo E2, Apo E3 and Apo E4 as described in Example 4.

As shown in FIG. 4, t-PA induced clot lysis is significantly (P±0.0001) enhanced by supplementation with Apo E2 ($EC_{50}$ of 0.20±0.06 μg/ml) as compared to t-PA alone (0.72±0.19). When Apo E4 is supplemented to the clot lysis assay, there is a significant (P<0.05) inhibition of clot lysis ($EC_{50}$ of 0.98±0.23 μg/ml) as compared to t-PA alone (0.72±0.19), but there is no significant change in t-PA induced clot lysis caused by Apo E3. Examining the relationship between patient genotypes and clot lysis, there is a significant increase in clot lysis for all groups with Apo E2 supplementation, and a nonsignificant trend for the Apo E4 patient group to have decreased clot lysis with Apo E3 and E4 supplementation. The results demonstrate that the t-PA is working through a clot degradation mechanism.

Figure 3B:
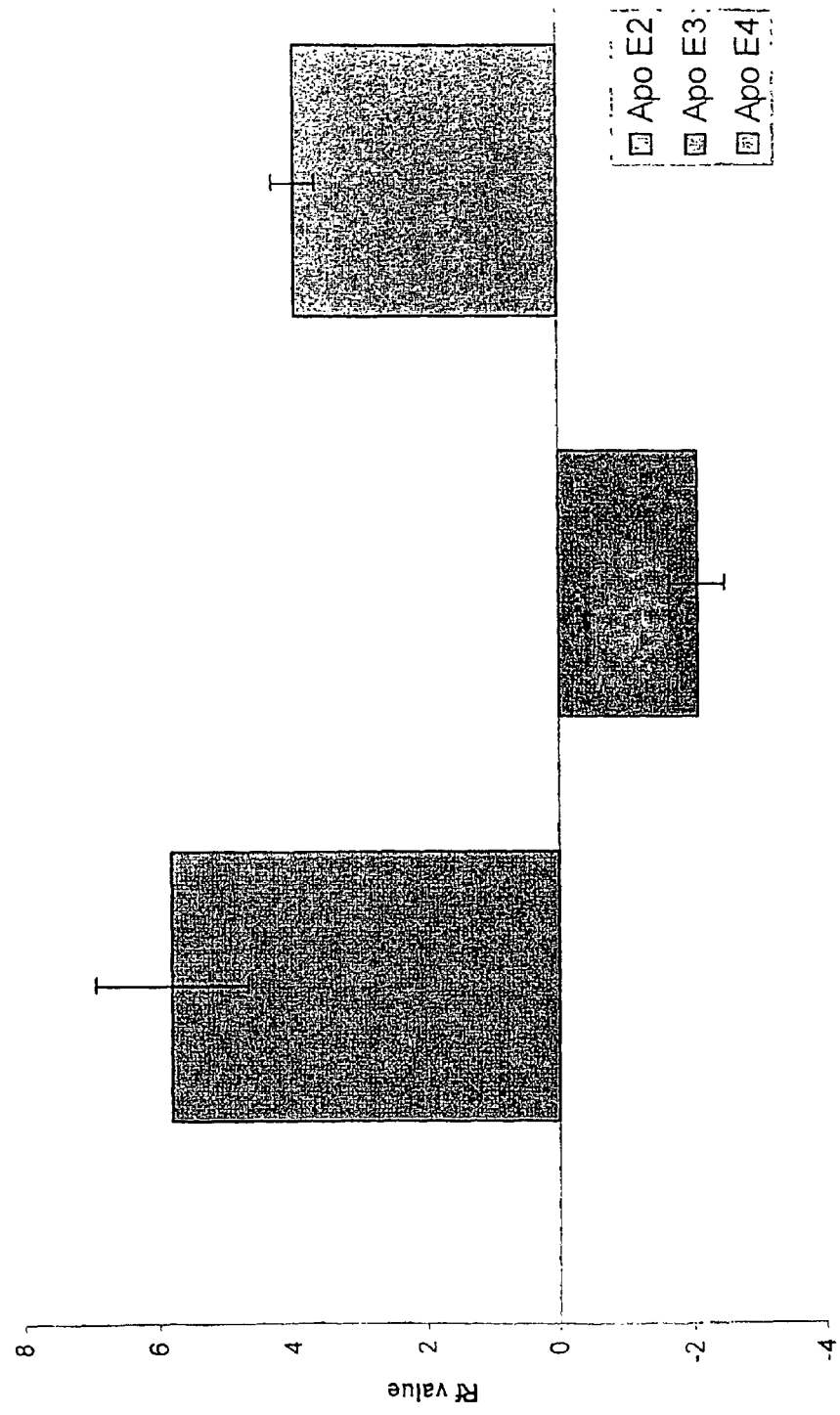

Using thin layer chromatography (TLC), as defined in Example 3, Apo E2 and E4 interacted chemically with t-PA, and Apo E3 either did not interact with t-PA or that said interaction is distinctly different than the interaction seen with E2 and E4 (as seen if FIG. 3b). The results demonstrate that Apo E2 reacts and uniquely binds with t-PA under the given conditions, through hydrophobic domains although the inventors do not intend to be bound by this theory.

The specific embodiments and examples set forth above are provided for illustrative purposes only and are not intended to limit the scope of the following claims. Additional embodiments of the invention and advantages provided thereby will be apparent to one of ordinary skill in the art and are within the scope of the claims.

What is claimed is:

1. A method for enhancing lysis of coagulated blood, comprising administering to coagulated blood a combination of a clot lysis agent and a lysis-enhancing amount of apolipoprotein E2 (Apo E2) or a therapeutic derivative thereof.

2. The method as defined by claim 1, wherein the clot lysis agent comprises tissue plasminogen activator (t-PA).

3. The method as defined by claim 1, wherein the clot lysis agent comprises a t-PA derivative.

4. The method as defined by claim 1, wherein a therapeutic derivative comprising fragments of Apo E2 having lysis-enhancing activity is administered.

5. The method as defined by claim 1, wherein the clot lysis agent comprises TNK-t-PA, t-PA, reteplase, streptokinase, heparin, coumadin, GIIb IIIa receptor blockers, therapeutic derivatives thereof, or mixtures thereof.

6. The method as defined by claim 1, wherein the clot lysis agent and the lysis-enhancing amount of Apo E2 are administered to reduce an individual's elevated level of coagulated blood.

7. The method as defined by claim 1, wherein the clot lysis agent and the lysis-enhancing amount of Apo E2 are administered to an individual with an ischemic disease.

8. The method as defined by claim 7, wherein the ischemic disease comprises myocardial infarction, unstable angina, coronary artery thrombus, or peripheral vascular disease.

9. The method as defined by claim 8, wherein the peripheral vascular disease comprises occlusion, retinopathy, or organ embolism.

10. The method as defined by claim 9, wherein the organ embolism comprises pulmonary embolism.

11. The method as defined by claim 1, wherein the clot lysis agent and the lysis-enhancing amount of Apo E2 are administered to an individual with post surgical complications of occlusion or clotting.

12. A method of reducing the risk of blood coagulation, comprising administering to blood a combination of a clot lysis agent and a lysis-enhancing amount of Apo E2 or a therapeutic derivative thereof.

13. The method as defined by claim 12, wherein the combination is administered to reduce the risk of the formation of an angiographic catheter clot.

* * * * *